(12) United States Patent
Jungwirth

(10) Patent No.: US 9,903,811 B2
(45) Date of Patent: Feb. 27, 2018

(54) MULTI-SPECTRAL REFLECTOMETER

(71) Applicant: THE BOEING COMPANY, Chicago, IL (US)

(72) Inventor: Douglas R. Jungwirth, Chicago, IL (US)

(73) Assignee: The Boeing Company, Chicago, IL (US)

(*) Notice: Subject to any disclaimer, the term of this patent is extended or adjusted under 35 U.S.C. 154(b) by 11 days.

(21) Appl. No.: 14/458,106

(22) Filed: Aug. 12, 2014

(65) Prior Publication Data

US 2016/0047742 A1   Feb. 18, 2016

(51) Int. Cl.
*G01J 3/46* (2006.01)
*G01N 21/47* (2006.01)
*G01N 33/32* (2006.01)

(52) U.S. Cl.
CPC ......... *G01N 21/4738* (2013.01); *G01N 33/32* (2013.01); *G01N 2021/4783* (2013.01)

(58) Field of Classification Search
CPC .. G01N 21/4738; G01N 21/25; G01N 21/293; G01N 33/32; G01N 2021/8427
See application file for complete search history.

(56) References Cited

U.S. PATENT DOCUMENTS

| 4,986,664 | A | * | 1/1991 | Lovoi | B23K 26/032 219/121.62 |
| 5,543,924 | A | * | 8/1996 | Surowiec | G01N 21/4738 356/446 |
| 6,052,191 | A | * | 4/2000 | Brayden, Jr. | G01B 11/0625 356/630 |
| 6,086,453 | A | * | 7/2000 | Fukuoka | G01N 21/9501 451/5 |
| 6,611,617 | B1 | * | 8/2003 | Crampton | G01B 11/2518 356/614 |
| 2003/0223072 | A1 | * | 12/2003 | Schulz | G01N 21/47 356/446 |
| 2005/0083346 | A1 | * | 4/2005 | Takahashi | H04N 1/6033 345/600 |
| 2010/0121607 | A1 | * | 5/2010 | Nabatova-Gabain | G01B 11/065 702/172 |
| 2011/0090492 | A1 | * | 4/2011 | Lemke | G01M 11/0278 356/239.2 |

(Continued)

*Primary Examiner* — Michael A Lyons
*Assistant Examiner* — Maurice Smith
(74) *Attorney, Agent, or Firm* — Haynes and Boone, LLP

(57) ABSTRACT

Systems, methods, and apparatus for determining an electromagnetic (EM) spectrum scattered from a surface are disclosed. The disclosed method involves scanning an EM source to at least one EM source position. The method further involves illuminating, with the EM source, spectral energy to at least one target area on the surface for each of the EM source positions. Also, the method involves scanning a detector to a plurality of detector positions for each of the EM source positions. Additionally, the method involves detecting, with the detector, the EM spectrum scattered from at least one target area on the surface at each of the plurality of the detector positions for each of the EM source positions. Further, the method involves processing the EM spectrum detected at each of the plurality of the detector positions for each of the EM source positions to characterize the surface.

20 Claims, 4 Drawing Sheets

(56) References Cited

U.S. PATENT DOCUMENTS

| | | | |
|---|---|---|---|
| 2012/0194820 A1* | 8/2012 | Kuo .................... | G01J 1/0242 356/446 |
| 2015/0192516 A1* | 7/2015 | Choulet ................ | G01N 21/86 356/445 |
| 2016/0150142 A1* | 5/2016 | Lapstun ................ | B64D 47/08 348/36 |

* cited by examiner

MULTI-SPECTRAL REFLECTOMETER

FIELD

The present disclosure relates to reflectometers. In particular, it relates to multi-spectral reflectometers.

BACKGROUND

In some applications, such as painting a large aircraft, large amounts of special effects paints and coatings are required to be applied to large surface areas of the object. When this process is not performed correctly, the expected "effect" (e.g., visual effect) is not achieved. In most cases, this error in the "effect" is not detected until after the paint has been dried and other additional processes have been performed to the coatings. In order to correct for this mistake, the painted object will need to be stripped and painted all over again.

As such, there is a need for a technique that allows for monitoring of the painting of an object at various stages of the application to verify that the expected effect is being achieved.

SUMMARY

The present disclosure relates to a method, system, and apparatus for a multi-spectral reflectometer. In one or more embodiments, a method for determining an electromagnetic (EM) spectrum scattered from a surface involves scanning an EM source to at least one EM source position. The method further involves illuminating, with the EM source, spectral energy to at least one target area on the surface for each of the EM source positions. Also, the method involves scanning a detector to a plurality of detector positions for each of the EM source positions. In addition, the method involves detecting, with the detector, the EM spectrum scattered from at least one target area on the surface at each of the plurality of the detector positions for each of the EM source positions. Further, the method involves processing, with at least one processor, the EM spectrum detected at each of the plurality of the detector positions for each of the EM source positions to characterize the surface.

In one or more embodiments, the surface is characterized in terms of color, irregularities of the surface, and/or bidirectional reflectance distribution function (BRDF).

In at least one embodiment, the EM source is a visible light source, an ultra violet (UV) source, an infrared (IR) source, and/or a radio frequency (RF) source. In some embodiments, the spectral energy has vertical polarization, horizontal polarization, right-hand (RH) polarization, and/or left-hand (LH) polarization.

In one or more embodiments, the detector is a visible light detector, an ultra violet (UV) detector, an infrared (IR) detector, and/or a radio frequency (RF) detector. In some embodiments, the detector detects vertical polarization, horizontal polarization, right-hand (RH) polarization, and/or left-hand (LH) polarization.

In at least one embodiment, the EM source is scanned in a horizontal scan and/or a vertical scan. In some embodiments, the EM source is scanned in a full two pi steradian.

In one or more embodiments, the detector is scanned in a horizontal scan and/or a vertical scan. In some embodiments, the detector is scanned in a full two pi steradian.

In at least one embodiment, a system for determining an electromagnetic (EM) spectrum scattered from a surface involves an EM source controller to scan an EM source to at least one EM source position. The system further involves the EM source to illuminate spectral energy to at least one target area on the surface for each of the EM source positions. Also, the system involves a detector controller to scan a detector to a plurality of detector positions for each of the EM source positions. In addition, the system involves the detector to detect the EM spectrum scattered from at least one target area on the surface at each of the plurality of the detector positions for each of the EM source positions. Further, the system involves at least one processor to process the EM spectrum detected at each of the plurality of the detector positions for each of the EM source positions to characterize the surface.

In one or more embodiments, the EM source controller and the detector controller are the same controller. In some embodiments, the EM source controller and the detector controller are different controllers.

The features, functions, and advantages can be achieved independently in various embodiments of the present inventions or may be combined in yet other embodiments.

DRAWINGS

These and other features, aspects, and advantages of the present disclosure will become better understood with regard to the following description, appended claims, and accompanying drawings where:

DESCRIPTION

Figure 1:
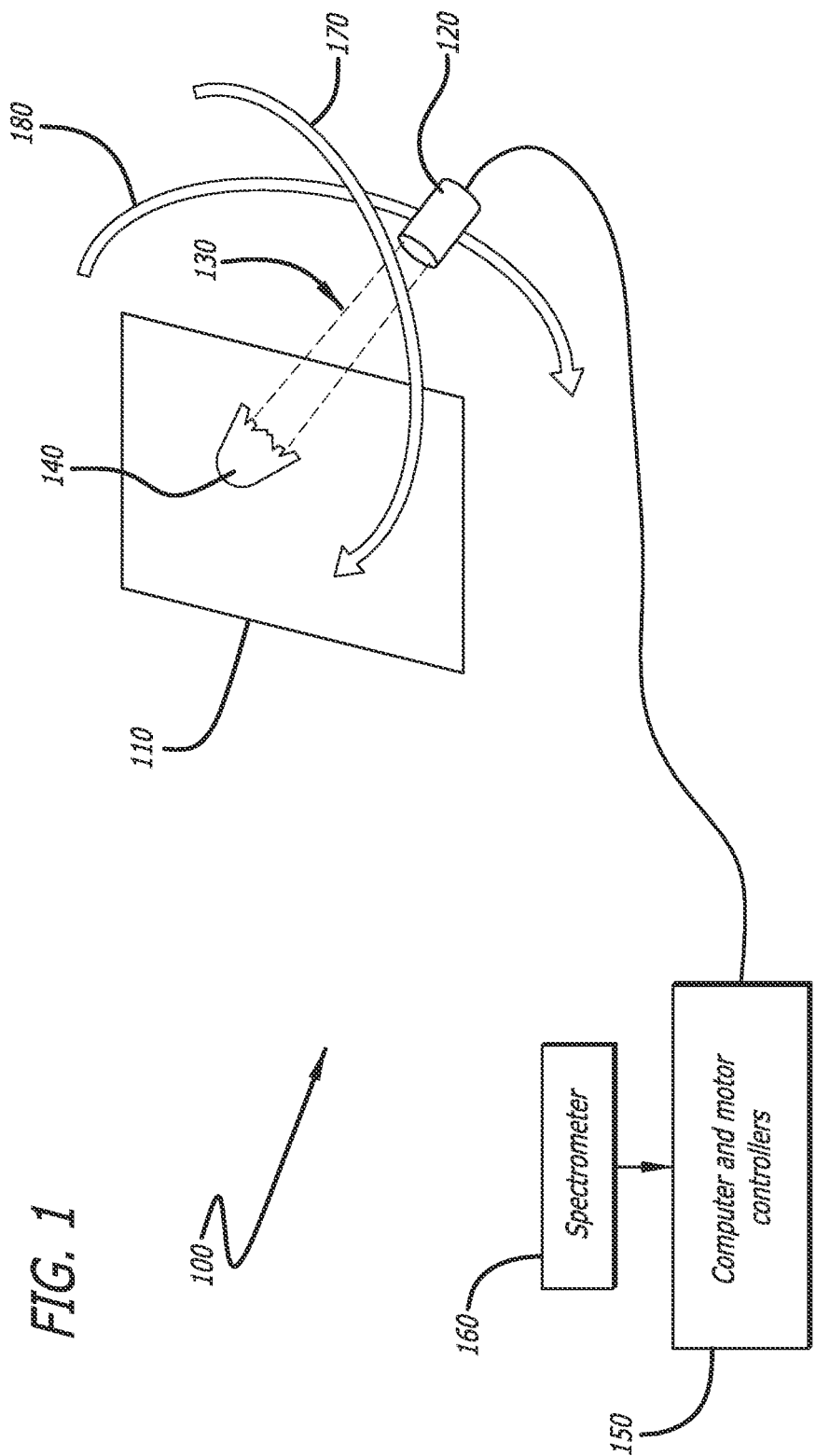
FIG. 1 is a diagram showing the illumination portion of the system for determining an electromagnetic (EM) spectrum scattered from a surface, in accordance with at least one embodiment of the present disclosure.

The methods and apparatus disclosed herein provide an operative system for for determining an electromagnetic (EM) spectrum scattered from a surface. The disclosed system, in one or more embodiments, measures the reflection (or scattering off) of a surface at various angles of incident illumination, at various angles of reflection, and over a desired EM spectrum. This data is used to calculate the expected reflection off of the measured surface for any "color" of incident light, at any illuminating angle, and at any viewing angle. This information can be used to perfect the application process of various inks, coatings, paints, surface finishes, etc. along with the verification of the proper "effect" that is expected from the surface finish.

As previously mentioned above, in some applications, for example, when painting a large aircraft, large amounts of special effects paints and coatings are required to be applied to large surface areas of the object. When this process is not performed correctly, the expected "effect" (e.g., visual effect) is not achieved. In most cases, this error in the "effect" is not detected until after the paint has been dried and other additional processes have been performed to the coatings. In order to correct for this mistake, the painted object will need to be stripped and painted all over again.

The disclosed system provides a numerical measurement that can be used to determine whether the application process has been completed correctly, and can predict mathematically what the actual "effect" will be for any combination of "color", illumination angle, and viewing angle. This accurate measurement process can be used, for example, for artistic painting of vehicles, optical stealth characteristics of military vehicles, and for anti-counterfeiting ink applications for documents.

In the following description, numerous details are set forth in order to provide a more thorough description of the system. It will be apparent, however, to one skilled in the art, that the disclosed system may be practiced without these specific details. In the other instances, well known features have not been described in detail so as not to unnecessarily obscure the system.

Embodiments of the invention may be described herein in terms of functional and/or logical block components and various processing steps. It should be appreciated that such block components may be realized by any number of hardware, software, and/or firmware components configured to perform the specified functions. For example, an embodiment of the invention may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present invention may be practiced in conjunction with, and that the system described herein is merely one example embodiment of the invention.

For the sake of brevity, conventional techniques and components related to signal processing, and other functional aspects of the system (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the invention.

FIG. 1 is a diagram 100 showing the illumination portion of the system for determining an electromagnetic (EM) spectrum scattered from a surface 110, in accordance with at least one embodiment of the present disclosure. In this figure, an EM source 120 is shown to be illuminating spectral energy 130 to a target area 140 on the surface 110.

Various different types of EM sources may be employed for the EM source 120 including, but not limited to, a visible light source, an ultra violet (UV) source, an infrared (IR) source, and/or a radio frequency (RF) source. In addition, the EM source 120 may radiate spectral energy 130 having various different polarizations including, but not limited to, vertical polarization, horizontal polarization, right-hand (RH) polarization, and/or left-hand (LH) polarization. Additionally, the surface 110 may be manufactured from various different materials including, but not limited to, metals, plastics, wood, and/or composite materials. In addition, the surface 110 may be treated and/or coated with various materials including primers, paints, and/or coatings (e.g., abrasion-resistant coatings).

Also in this figure, the EM source 120 is connected (by wire and/or wirelessly) to a computer and a motor controller (i.e. an EM source controller and/or a detector controller) 150. The computer and motor controller 150 are connected (by wire and/or wirelessly) to a spectrometer 160. It should be noted that in some embodiments, the EM source controller and the detector controller are different controllers, and in other embodiments, they are the same controller.

Figure 2:
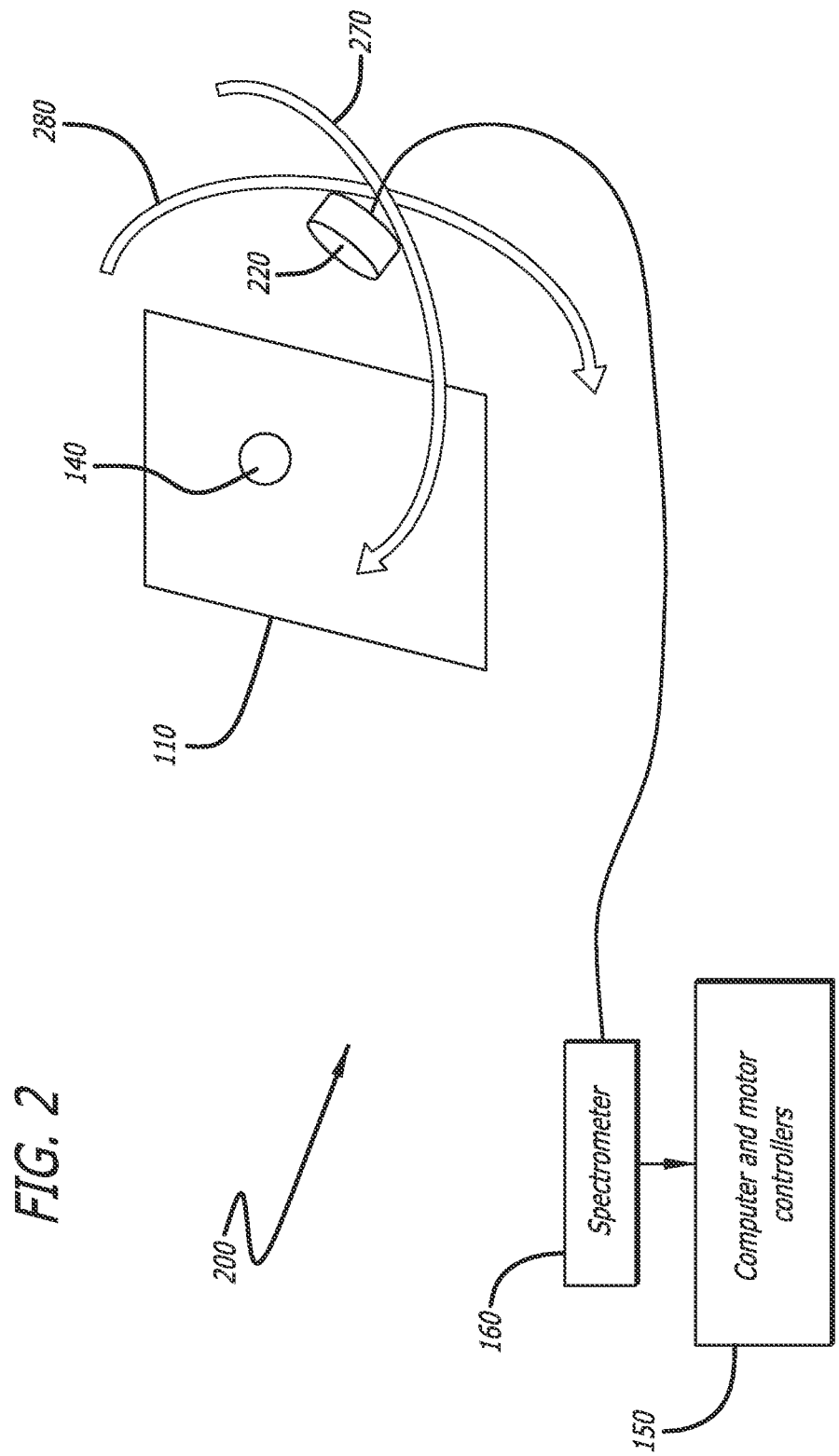
FIG. 2 is a diagram showing the measuring portion of the system for determining an electromagnetic (EM) spectrum scattered from a surface, in accordance with at least one embodiment of the present disclosure.

FIG. 2 is a diagram 200 showing the measuring portion of the system for determining an electromagnetic (EM) spectrum scattered from a surface 110, in accordance with at least one embodiment of the present disclosure. In this figure, a detector 220 is shown to be detecting the EM spectrum scattered from the target area 140 on the surface 110.

In one or more embodiments, the detector 220 may employ an integrating sphere with an imaging lens; however, the detector 220 may be manufactured to employ various different optical elements. In addition, different types of EM detectors may be employed for the detector 220 including, but not limited to, a visible light detector, an ultra violet (UV) detector, an infrared (IR) detector, and/or a radio frequency (RF) detector. In addition, the detector 220 may detect scattered EM spectrums having various different polarizations including, but not limited to, vertical polarization, horizontal polarization, right-hand (RH) polarization, and/or left-hand (LH) polarization. Additionally, the detector 220 is connected (by wire and/or wirelessly) to the spectrometer 160. The spectrometer is connected (by wire and/or wirelessly) to the computer and the motor controller (i.e. an EM source controller and/or a detector controller) 150.

During operation of the disclosed system, the EM source 120 is scanned (e.g., moved), by the motor controller (e.g., an EM source controller) 150, to a first EM source position such that the EM source 120 is able to illuminate the target area 140 on the surface 110. When the EM source 120 is located in the first EM source position, the EM source 120 illuminates spectral energy 130 to the target area 140 on the surface 110.

The detector 220 is scanned (e.g., moved), by the motor controller (e.g., a detector controller) 150, to a first detector position such that the detector 220 is able to detect the EM spectrum scattered from the target area 140 on the surface 110. When the detector 220 is located in the first detector position, the detector 220 detects the EM spectrum scattered from the target area 140 on the surface 110. The detector 220 sends the detected information to the spectrometer 160, which determines the EM spectrum detected. The spectrometer 160 then sends the EM spectrum information to the computer 150 for processing.

Then, while the EM source 120 is still located in the first EM source position and is still illuminating spectral energy 130 to the target area 140 on the surface 110, the detector 220 is scanned (e.g., moved), to a second detector position such that the detector 220 is able to detect the EM spectrum scattered from the target area 140 on the surface 110. When the detector 220 is located in the second detector position, the detector 220 detects the EM spectrum scattered from the target area 140 on the surface 110. The detector 220 sends the detected information to the spectrometer 160, which determines the EM spectrum detected. The spectrometer 160 then sends the EM spectrum information to the computer 150 for processing.

While the EM source 120 is still located in the first EM source position and is still illuminating spectral energy 130 to the target area 140 on the surface 110, the detector 220 is scanned (e.g., moved), to another detector position, and the process repeats for as many different detector positions as desired. In one or more embodiments, the detector 220 is scanned in a horizontal scan 270 and/or a vertical scan 280. In some embodiments, the detector 220 is scanned in a full two pi (π) steradian.

Then, after the detector has been scanned to the number of desired detector positions, the EM source 120 is scanned (e.g., moved), by the motor controller (e.g., an EM source controller) 150, to a second EM source position such that the EM source 120 is able to illuminate the target area 140 on the surface 110. When the EM source 120 is located in the second EM source position, the EM source 120 illuminates spectral energy 130 to the target area 140 on the surface 110.

The detector 220 is scanned (e.g., moved), by the motor controller (e.g., a detector controller) 150, to the first detector position such that the detector 220 is able to detect the EM spectrum scattered from the target area 140 on the surface 110. When the detector 220 is located in the first detector position, the detector 220 detects the EM spectrum scattered from the target area 140 on the surface 110. The detector 220 sends the detected information to the spectrometer 160, which determines the EM spectrum detected. The spectrometer 160 then sends the EM spectrum information to the computer 150 for processing.

Then, while the EM source 120 is still located in the second EM source position and is still illuminating spectral energy 130 to the target area 140 on the surface 110, the detector 220 is scanned (e.g., moved), to the second detector position such that the detector 220 is able to detect the EM spectrum scattered from the target area 140 on the surface 110. When the detector 220 is located in the second detector position, the detector 220 detects the EM spectrum scattered from the target area 140 on the surface 110. The detector 220 sends the detected information to the spectrometer 160, which determines the EM spectrum detected. The spectrometer 160 then sends the EM spectrum information to the computer 150 for processing.

While the EM source 120 is still located in the second EM source position and is still illuminating spectral energy 130 to the target area 140 on the surface 110, the detector 220 is scanned (e.g., moved), to another detector position, and the process repeats for as many different detector positions as desired.

Then, after the detector 220 has been scanned to the number of desired detector positions, the EM source 120 is scanned (e.g., moved), by the motor controller (e.g., an EM source controller) 150, to another EM source position such that the EM source 120 is able to illuminate the target area 140 on the surface 110, and the entire process repeats for as many different EM source positions as desired.

In one or more embodiments, the EM source 120 is scanned in a horizontal scan 170 and/or a vertical scan 180. In some embodiments, the EM source 120 is scanned in a full two pi (π) steradian.

After the entire process has repeated for the number of desired EM source positions (or during the process), the computer 150 processes the EM spectrum detected by the detector 220 at each of the detector positions for each of the EM source positions to characterize the surface 110. The computer 150 characterizes the surface 110 in terms of its color, irregularities of the surface 110, and/or the bidirectional reflectance distribution function (BRDF). In one or more embodiments, the computer 150 may characterize the surface 110 in terms of its color by determining the numerical value for the amount of scattered EM spectrum for each wavelength, for each of the detector positions for each of the EM source positions. For example, for when the EM source 120 is in the first EM source position and the detector 220 is in the first detector position, the computer 150 may determine from the reflected EM spectrum that the color of the surface 110 exhibits 30% of green, 40% of blue, and 30% of red.

Figure 3:
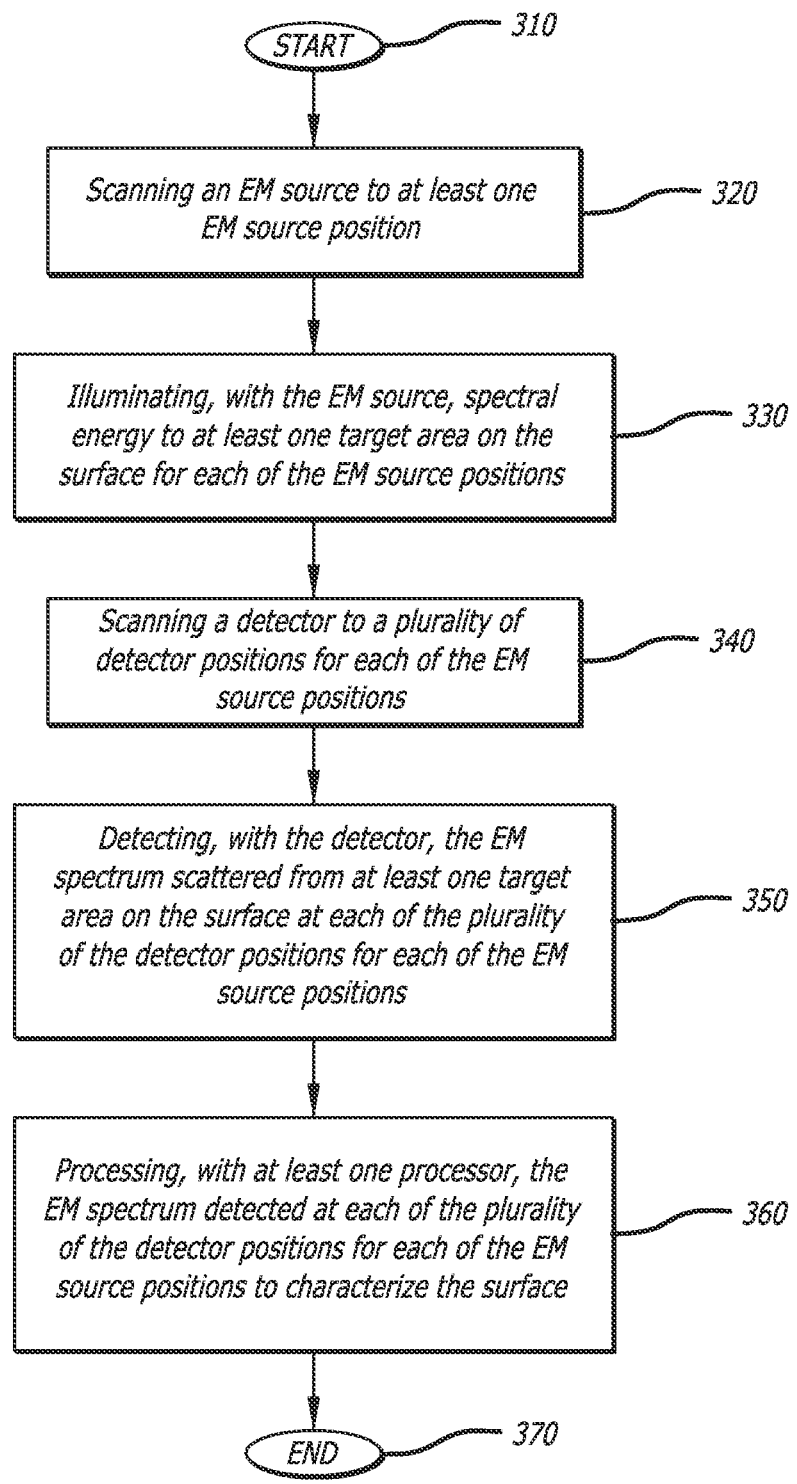
FIG. 3 depicts a flow chart showing the method for determining an electromagnetic (EM) spectrum scattered from a surface, in accordance with at least one embodiment of the present disclosure.

FIG. 3 depicts a flow chart showing the method 300 for determining an electromagnetic (EM) spectrum scattered from a surface, in accordance with at least one embodiment of the present disclosure. At the start 310 of the method 300, an EM source is scanned to at least one EM source position 320. The EM source illuminates spectral energy to at least one target area on the surface for each of the EM source positions 330. A detector is scanned to a plurality of detector positions for each of the EM source positions 340. The detector detects the EM spectrum scattered from at least one target area on the surface at each of the plurality of the detector positions for each of the EM source positions 350. Then, at least one processor processes the EM spectrum detected at each of the plurality of the detector positions for each of the EM source positions to characterize the surface 360. Then, the method 300 ends 370.

Figure 4:
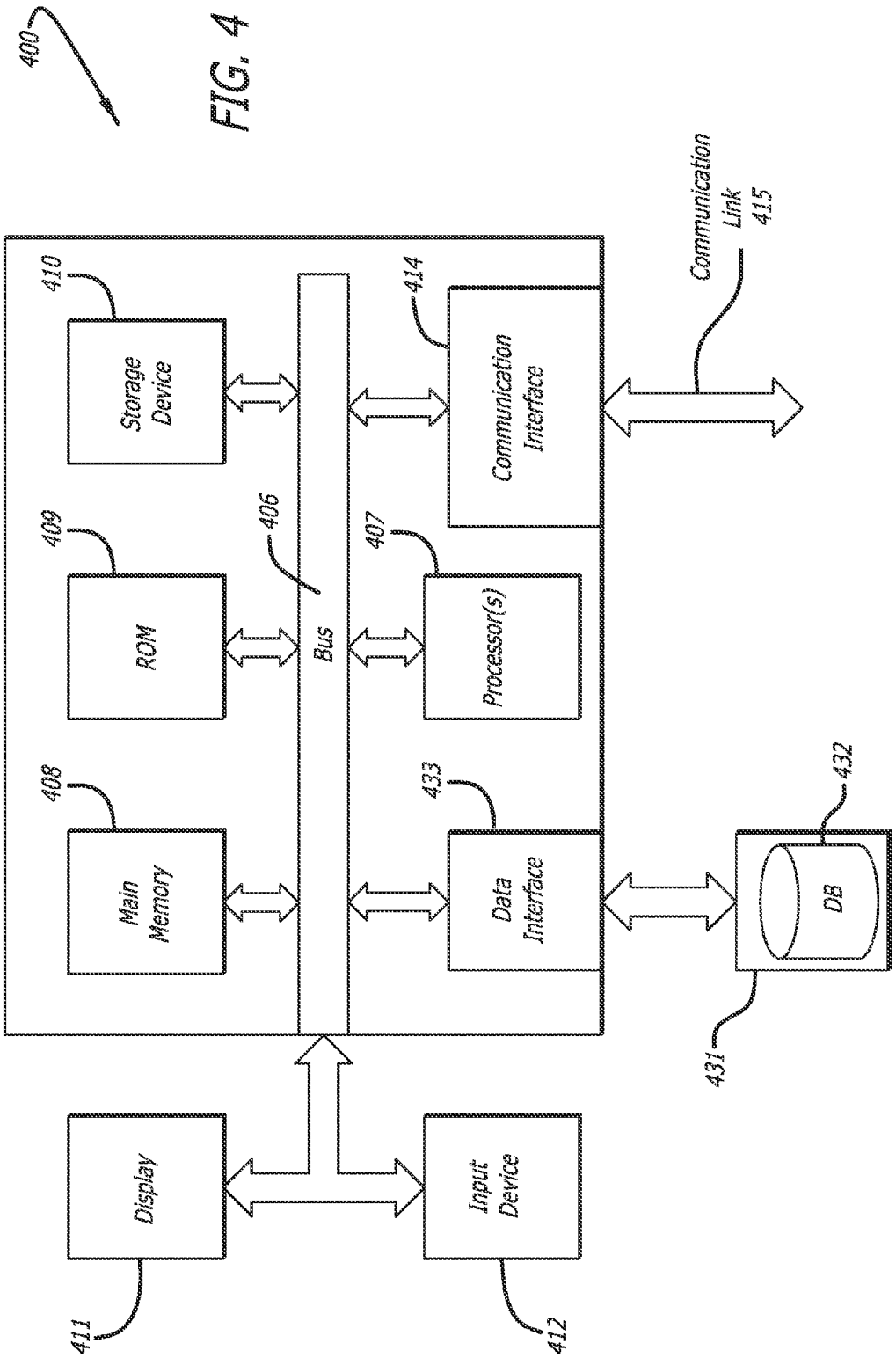
FIG. 4 illustrates a block diagram of an illustrative computing system suitable for implementing an embodiment of the present disclosure, in accordance with at least one embodiment of the present disclosure.

FIG. 4 illustrates a block diagram of an illustrative computing system 400 suitable for implementing an embodiment of the present disclosure. For example, the computer 150 in FIGS. 1 and 2 (e.g., which may include and/or employ at least one processor) may include and/or employ at least a portion of the disclosed computer system 400. Computing system 400 includes a bus 406 or other communication mechanism for communicating information, which interconnects subsystems and devices, such as processor 407, system memory 408 (e.g., RAM), static storage device 409 (e.g., ROM), disk drive 410 (e.g., magnetic or optical), communication interface 414 (e.g., modem or Ethernet card), display 411 (e.g., CRT or LCD), input device 412 (e.g., keyboard), and cursor control (not shown).

According to one embodiment of the present disclosure, computer system 400 performs specific operations by processor 407 executing one or more sequences of one or more instructions contained in system memory 408. Such instructions may be read into system memory 408 from another computer readable/usable medium, such as static storage device 409 or disk drive 410. In alternative embodiments, hard-wired circuitry may be used in place of or in combination with software instructions to implement the present disclosure. Thus, embodiments of the present disclosure are not limited to any specific combination of hardware circuitry and/or software. In one embodiment, the term "logic" shall mean any combination of software or hardware that is used to implement all or part of the present disclosure.

The term "computer readable medium" or "computer usable medium" as used herein refers to any medium that participates in providing instructions to processor 407 for execution. Such a medium may take many forms, including but not limited to, non-volatile media, volatile media, and transmission media. Non-volatile media includes, for example, optical or magnetic disks, such as disk drive 410. Volatile media includes dynamic memory, such as system memory 408.

Common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, or any other medium from which a computer can read.

In an embodiment of the present disclosure, execution of the sequences of instructions to practice the present disclosure is performed by a single computer system 400. According to other embodiments of the present disclosure, two or more computer systems 400 coupled by communication link 415 (e.g., LAN, PTSN, or wireless network) may perform the sequence of instructions required to practice the present disclosure in coordination with one another.

Computer system 400 may transmit and receive messages, data, and instructions, including program, i.e., application code, through communication link 415 and communication interface 414. Received program code may be executed by processor 407 as it is received, and/or stored in disk drive 410, or other non-volatile storage for later execution. Computer system 400 may also interact with a database 432 within a database system 431 via a data interface 433 where the computer system 400 may store and retrieve information or data of the electronic design into and from the database system 431.

Although particular embodiments have been shown and described, it should be understood that the above discussion is not intended to limit the scope of these embodiments. While embodiments and variations of the many aspects of the invention have been disclosed and described herein, such disclosure is provided for purposes of explanation and illustration only. Thus, various changes and modifications may be made without departing from the scope of the claims.

Where methods described above indicate certain events occurring in certain order, those of ordinary skill in the art having the benefit of this disclosure would recognize that the ordering may be modified and that such modifications are in accordance with the variations of the invention. Additionally, parts of methods may be performed concurrently in a parallel process when possible, as well as performed sequentially. In addition, more parts or less part of the methods may be performed.

Accordingly, embodiments are intended to exemplify alternatives, modifications, and equivalents that may fall within the scope of the claims.

Although certain illustrative embodiments and methods have been disclosed herein, it can be apparent from the foregoing disclosure to those skilled in the art that variations and modifications of such embodiments and methods can be made without departing from the true spirit and scope of the art disclosed. Many other examples of the art disclosed exist, each differing from others in matters of detail only. Accordingly, it is intended that the art disclosed shall be limited only to the extent required by the appended claims and the rules and principles of applicable law.

I claim:

1. A method for determining a visual effect of a surface by determining an electromagnetic (EM) spectrum scattered from the surface, the method comprising:
    scanning an EM source to a plurality of EM source positions;
    illuminating, with the EM source, spectral energy to at least one target area on the surface for each of the EM source positions;
    for each one of the EM source positions, scanning a detector to a plurality of different detector positions, wherein at least two of the plurality of different detector positions are on a different scan axis;
    detecting, with the detector, the EM spectrum scattered from the at least one target area on the surface at each of the plurality of the detector positions for each of the EM source positions; and
    processing, with at least one processor, the EM spectrum detected at each of the plurality of the detector positions for each of the EM source positions to determine a visual effect of the surface by characterizing the surface in terms of its color by an amount of the EM spectrum scattered for each wavelength, for each of the detector positions for each of the EM source positions.

2. The method of claim 1, wherein the surface is further characterized in terms of at least one of irregularities of the surface or bidirectional reflectance distribution function (BRDF).

3. The method of claim 1, wherein the EM source is at least one of a visible light source, an ultra violet (UV) source, an infrared (IR) source, and a radio frequency (RF) source.

4. The method of claim 1, wherein the spectral energy has at least one of vertical polarization, horizontal polarization, right-hand (RH) polarization, and left-hand (LH) polarization.

5. The method of claim 1, wherein the detector is at least one of a visible light detector, an ultra violet (UV) detector, an infrared (IR) detector, and a radio frequency (RF) detector.

6. The method of claim 1, wherein the detector detects at least one of vertical polarization, horizontal polarization, right-hand (RH) polarization, and left-hand (LH) polarization.

7. The method of claim 1, wherein the EM source is scanned in at least one of a horizontal scan and a vertical scan.

8. The method of claim 1, wherein the EM source is scanned in a full two pi steradian.

9. The method of claim 1, wherein the detector is scanned in at least one of a horizontal scan and a vertical scan.

10. The method of claim 1, wherein the detector is scanned in a full two pi steradian.

11. A system for determining a visual effect of a surface by determining an electromagnetic (EM) spectrum scattered from the surface, the system comprising:
    an EM source controller to scan an EM source to a plurality of EM source positions;
    the EM source to illuminate spectral energy to at least one target area on the surface for each of the EM source positions;
    for each one of the EM source positions, a detector controller to scan a detector to a plurality of different detector positions, wherein at least two of the plurality of different detector positions are on a different scan axis;
    the detector to detect the EM spectrum scattered from the at least one target area on the surface at each of the plurality of the detector positions for each of the EM source positions; and
    at least one processor to process the EM spectrum detected at each of the plurality of the detector positions for each of the EM source positions to determine a visual effect of the surface by characterizing the surface in terms of its color by an amount of the EM spectrum scattered for each wavelength, for each of the detector positions for each of the EM source positions.

12. The system of claim 11, wherein the surface is further characterized in terms of at least one of irregularities of the surface or bidirectional reflectance distribution function (BRDF).

13. The system of claim 11, wherein the EM source is at least one of a visible light source, an ultra violet (UV) source, an infrared (IR) source, and a radio frequency (RF) source.

14. The system of claim 11, wherein the spectral energy has at least one of vertical polarization, horizontal polarization, right-hand (RH) polarization, and left-hand (LH) polarization.

15. The system of claim 11, wherein the detector is at least one of a visible light detector, an ultra violet (UV) detector, an infrared (IR) detector, and a radio frequency (RF) detector.

16. The system of claim 11, wherein the detector detects at least one of vertical polarization, horizontal polarization, right-hand (RH) polarization, and left-hand (LH) polarization.

17. The system of claim 11, wherein the EM source is scanned in at least one of a horizontal scan and a vertical scan.

18. The system of claim 11, wherein the detector is scanned in at least one of a horizontal scan and a vertical scan.

19. The system of claim 11, wherein the EM source controller and the detector controller are a same controller.

20. The system of claim 11, wherein the EM source controller and the detector controller are different controllers.

* * * * *